United States Patent
Yabuguchi et al.

(10) Patent No.: US 10,945,890 B2
(45) Date of Patent: Mar. 16, 2021

(54) MANUFACTURING METHOD FOR ABSORBING BODY

(71) Applicant: SUMITOMO SEIKA CHEMICALS CO., LTD., Hyogo (JP)

(72) Inventors: Hiroki Yabuguchi, Himeji (JP); Toru Kawahara, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 15/751,776

(22) PCT Filed: Aug. 10, 2016

(86) PCT No.: PCT/JP2016/073646
§ 371 (c)(1),
(2) Date: Feb. 9, 2018

(87) PCT Pub. No.: WO2017/026530
PCT Pub. Date: Feb. 16, 2017

(65) Prior Publication Data
US 2018/0353349 A1  Dec. 13, 2018

(30) Foreign Application Priority Data

Aug. 12, 2015 (JP) .............................. JP2015-159559

(51) Int. Cl.
*A61F 13/15* (2006.01)
*A61F 13/539* (2006.01)
(Continued)

(52) U.S. Cl.
CPC ........ *A61F 13/15658* (2013.01); *A61F 13/15* (2013.01); *A61F 13/15707* (2013.01);
(Continued)

(58) Field of Classification Search
CPC .......... A61F 13/15658; A61F 13/15764; A61F 13/539; A61F 13/15; A61F 13/15617;
(Continued)

(56) References Cited

U.S. PATENT DOCUMENTS

| | | | |
|---|---|---|---|
| 2,983,303 A | * | 5/1961 | Voss ........................ B29B 11/16 264/115 |
| 4,610,678 A | | 9/1986 | Weisman et al. |

(Continued)

FOREIGN PATENT DOCUMENTS

| CN | 101277663 A | 10/2008 |
|---|---|---|
| EP | 1 943 991 A1 | 7/2008 |

(Continued)

OTHER PUBLICATIONS

Machine Translation of JP-2010-035701 (Year: 2010).*
(Continued)

*Primary Examiner* — Mark A Osele
*Assistant Examiner* — Christopher C Caillouet
(74) *Attorney, Agent, or Firm* — Knobbe, Martens, Olson & Bear, LLP (57) ABSTRACT

A method for manufacturing an absorbent body according to the present invention includes a first step of successively introducing an aggregate of absorbent fibers and a water-absorbent resin into a gap that is formed between a first surface and a second surface and is smaller than a thickness of the aggregate of the absorbent fibers, recesses and protrusions being formed on at least one of the first surface and the second surface, a second step of applying a shearing force to the aggregate of the absorbent fibers by moving the first surface relative to and parallel to the second surface in order to mix the absorbent fibers and the water-absorbent resin, and a third step of causing the absorbent fibers and the water-absorbent resin that were mixed to fall, and stacking
(Continued)

the absorbent fibers and the water-absorbent resin by suctioning the absorbent fibers and the water-absorbent resin into a recessed portion having a predetermined shape.

13 Claims, 6 Drawing Sheets

(51) Int. Cl.
  *A61F 13/53* (2006.01)
  *A61F 13/534* (2006.01)
  *A61F 13/84* (2006.01)
(52) U.S. Cl.
  CPC ...... *A61F 13/15764* (2013.01); *A61F 13/539* (2013.01); *A61F 2013/530131* (2013.01); *A61F 2013/53445* (2013.01); *A61F 2013/8488* (2013.01); *Y10T 156/1057* (2015.01)
(58) Field of Classification Search
  CPC ... A61F 2013/530131; Y10T 156/1057; Y10T 156/1062
  See application file for complete search history.

(56) References Cited

U.S. PATENT DOCUMENTS

| | | | |
|---|---|---|---|
| 4,674,966 A | 6/1987 | Johnson et al. | |
| 4,921,659 A | 5/1990 | Marshall et al. | |
| 5,314,126 A * | 5/1994 | Alvarez | B02C 13/04 241/189.1 |
| 5,316,601 A * | 5/1994 | Hebbard | A61F 13/15617 156/62.2 |
| 6,982,052 B2 * | 1/2006 | Daniels | A61F 13/15203 264/101 |
| 9,943,446 B2 * | 4/2018 | Jackels | A61F 13/15626 |
| 2003/0044562 A1 * | 3/2003 | Li | A01K 1/0152 428/59 |
| 2007/0250026 A1 | 10/2007 | Venturino et al. | |
| 2009/0212262 A1 * | 8/2009 | Elson | C02F 1/4691 252/500 |
| 2009/0281511 A1 | 11/2009 | Fukae | |
| 2013/0289509 A1 | 10/2013 | Mukai et al. | |
| 2014/0004326 A1 * | 1/2014 | Petersen | D04H 1/425 428/219 |

FOREIGN PATENT DOCUMENTS

| | | |
|---|---|---|
| JP | 4115077 B2 | 7/2008 |
| JP | 2010-035701 A | 2/2010 |
| JP | 2011-083545 A | 4/2011 |
| JP | 2012-139381 A | 7/2012 |
| JP | 2014-014667 A | 1/2014 |
| JP | 2015-066013 A | 4/2015 |
| WO | WO 2015/079964 A1 | 6/2015 |

OTHER PUBLICATIONS

Extended European Search Report in corresponding European Application No. EP 16 83 5227, dated Feb. 28, 2019.
Examination Report, corresponding Chinese Patent Application No. 201680044424.5, dated May 13, 2020.

* cited by examiner

| Absorbent piece | Sample 1 | | | | | | | Sample 2 | | | | | | |
|---|---|---|---|---|---|---|---|---|---|---|---|---|---|---|
| | C (g) | D (g) | X | | Y | | | C (g) | D (g) | X | | Y | | |
| | | | (g) | Deviation | (g) | Deviation | | | | (g) | Deviation | (g) | Deviation |
| 1 | 2.24 | 411 | 1.11 | 0.01 | 1.13 | 0.02 | | 2.14 | 396 | 1.07 | -0.02 | 1.07 | -0.02 |
| 2 | 2.16 | 397 | 1.07 | -0.03 | 1.09 | -0.02 | | 2.17 | 407 | 1.10 | 0.01 | 1.07 | -0.02 |
| 3 | 2.15 | 403 | 1.09 | -0.01 | 1.06 | -0.05 | | 2.18 | 397 | 1.07 | -0.02 | 1.11 | 0.02 |
| 4 | 2.20 | 404 | 1.09 | -0.01 | 1.11 | 0.00 | | 2.18 | 407 | 1.10 | 0.01 | 1.08 | -0.01 |
| 5 | 2.29 | 426 | 1.15 | 0.05 | 1.14 | 0.03 | | 2.24 | 425 | 1.15 | 0.06 | 1.09 | 0.00 |
| 6 | 2.23 | 411 | 1.11 | 0.01 | 1.12 | 0.01 | | 2.27 | 415 | 1.12 | 0.03 | 1.15 | 0.06 |
| 7 | 2.23 | 415 | 1.12 | 0.02 | 1.11 | 0.00 | | 2.17 | 400 | 1.08 | -0.01 | 1.09 | 0.00 |
| 8 | 2.16 | 400 | 1.08 | -0.02 | 1.08 | -0.03 | | 2.17 | 407 | 1.10 | 0.01 | 1.07 | -0.02 |
| 9 | 2.19 | 397 | 1.07 | -0.03 | 1.12 | 0.01 | | 2.15 | 390 | 1.05 | -0.04 | 1.10 | 0.01 |
| Total | 19.85 | 3663 | 9.89 | | 9.96 | | | 19.67 | 3644 | 9.84 | | 9.83 | |

MANUFACTURING METHOD FOR ABSORBING BODY

TECHNICAL FIELD

The present invention relates to a method for manufacturing an absorbent body.

BACKGROUND ART

Hygienic articles such as disposable diapers and sanitary items have absorbent bodies obtained by mixing absorbent fibers and water-absorbent resin. The water-absorbent resin used therein needs to be evaluated for various items in accordance with its application, and examples of evaluation items are various and include absorption capacity, absorption speed, absorption capacity under pressure, and gel strength. Also, as one evaluation of the water-absorbent resin, it is preferable to produce an absorbent body that is equivalent to the actual product as a test piece. Various techniques have been proposed, such as Patent Literature 1, for example, as techniques for manufacturing such an absorbent body.

CITATION LIST

Patent Literature

Patent Literature 1: JP 2011-83545A

SUMMARY OF INVENTION

Technical Problem

However, an apparatus disclosed in Patent Literature 1 is for manufacturing a large number of absorbent bodies as actual products, and thus this apparatus is large-scale, and the absorbent bodies cannot be manufactured unless a large amount of absorbent fibers and water-absorbent resin is used. Therefore, this apparatus is not appropriate for production of an absorbent body for testing. Also, the apparatus that is disclosed in Patent Literature 1 and manufactures the same type of product in a large amount is not appropriate in light of the fact that absorbent bodies for testing need to be modified as appropriate in accordance with the evaluation content such as the weight or the blending ratio of the absorbent fibers and the water-absorbent resin.

The present invention was made in order to solve this problem, and an object of the present invention is to provide a method for manufacturing an absorbent body in which absorbent fibers and water-absorbent resin are mixed similarly to the actual product and the composition such as the blending ratio of these absorbent fibers and water-absorbent resin can be easily changed.

Solution to Problem

A method for manufacturing an absorbent body according to the present invention includes a first step of successively introducing an aggregate of absorbent fibers and a water-absorbent resin into a gap that is formed between a first surface and a second surface and is smaller than a thickness of the aggregate of the absorbent fibers, recesses and protrusions being formed on at least one of the first surface and the second surface, a second step of applying a shearing force to the aggregate of the absorbent fibers by moving the first surface relative to and parallel to the second surface in order to mix the absorbent fibers and the water-absorbent resin, and a third step of causing the absorbent fibers and the water-absorbent resin that were mixed to fall, and stacking the absorbent fibers and the water-absorbent resin by suctioning the absorbent fibers and the water-absorbent resin into a recessed portion having a predetermined shape.

In the above-described method for manufacturing an absorbent body, in the first step, the water-absorbent resin can be dispersively disposed in contact with the aggregate of the absorbent fibers. At this time, the water-absorbent resin that is dispersively disposed in contact with the aggregate of the absorbent fibers can be dispersively disposed on an upper surface of the absorbent fibers.

Also, in the above-described method for manufacturing an absorbent body, in the first step, the water-absorbent resin can be introduced into the gap at a time that is different from a time at which the aggregate of the absorbent fibers is introduced.

In the method for manufacturing an absorbent body, after the aggregate of the absorbent fibers and the water-absorbent resin are moved along the gap by a predetermined distance in the second step, the absorbent fibers and the water-absorbent resin that were mixed can be caused to fall in the third step.

In the method for manufacturing an absorbent body, a configuration is possible in which recesses and protrusions are formed on the first surface, and recesses and protrusions are formed on the second surface on a downstream side in a direction in which the aggregate of the absorbent fibers and the water-absorbent resin move.

In the method for manufacturing an absorbent body, a through hole can be formed in the second surface on a downstream side in a direction in which the aggregate of the absorbent fibers and the water-absorbent resin move, and the absorbent fibers and the water-absorbent resin that were mixed can be caused to fall from the through hole in the third step.

In the method for manufacturing an absorbent body, the first surface can be formed by an outer circumferential surface of a rotatable cylindrical body, and the second surface can be disposed facing the outer circumferential surface of the cylindrical body.

In the method for manufacturing an absorbent body, the through hole can be formed at a site on the second surface that is positioned below the cylindrical body, and the absorbent fibers and the water-absorbent resin that were mixed can be caused to fall from the through hole in the third step.

In the method for manufacturing an absorbent body, the absorbent fibers and the water-absorbent resin that were mixed in a closed space can be caused to fall in the third step.

In the method for manufacturing an absorbent body, a shape of the space can increase in size toward its lower end, and the recessed portion can be formed into a shape corresponding to the shape of the lower end of the space.

In the method for manufacturing an absorbent body, a size of the absorbent body can be 15 cm×10 cm to 80 cm×30 cm.

A method for evaluating a water-absorbent resin according to the present invention includes a step of manufacturing an absorbent body using any of the above-described methods for manufacturing an absorbent body and a step of measuring a property of the absorbent body.

In the method for evaluating an water-absorbent resin, the property of the absorbent body can be at least one of the group consisting of a permeation time, a return amount, a diffusion length, an absorption capacity, and a dispersion state of the absorbent body.

In the method for evaluating a water-absorbent resin, in the step of manufacturing the absorbent body, a required amount of the water-absorbent resin for evaluation can be 1 g to 100 g.

Advantageous Effects of Invention

According to a method for manufacturing an absorbent body according to the present invention, absorbent fibers and water-absorbent resin are mixed similarly to an actual product, and it is possible to easily change the composition such as the blending ratio of these absorbent fibers and water-absorbent resin.

DESCRIPTION OF EMBODIMENTS

Hereinafter, a method for manufacturing an absorbent body according to the present invention will be described. In the present embodiment, a material body having an aggregate of absorbent fibers and water-absorbent resin is prepared, and an absorbent body in which the absorbent fibers and the water-absorbent resin are uniformly mixed is manufactured. Therefore, in the present embodiment, before the manufacture, a body containing an aggregate of absorbent fibers and water-absorbent resin is referred to as a "material body", and a body obtained by mixing the absorbent fibers and the water-absorbent resin is referred to as an "absorbent body". However, the expression "uniformly mixed" above is merely an expression indicating a state in which the absorbent fibers and the water-absorbent resin are mixed sufficiently, and does not necessarily mean that the abundance ratio of the absorbent fibers and the water-absorbent resin is constant in all of the sites of the absorbent body. For example, an absorbent body in which the abundance ratio of the water-absorbent resin and the absorbent fibers varies between the lower portion and the upper portion of the absorbent body. Note that the modes of the material body are various and thus will be described later. Hereinafter, first, materials that constitute the absorbent body and the material body will be described, and thereafter, a specific method for manufacturing the absorbent body will be described.

1. Absorbent Body and Material Body

As described above, the absorbent body and the material body according to the present embodiment include absorbent fibers and water-absorbent resin. Hereinafter, these will be described in detail.

(1-1) Absorbent Fibers

Hydrophilic fibers that were finely cut and crushed can be used as the absorbent fibers, for example. Examples of the hydrophilic fibers include cellulose fiber obtained from wood, such as cotton-like pulp, mechanical pulp, chemical pulp, and semi-chemical pulp; artificial cellulose fiber such as rayon and acetate; and fibers made of synthetic resin that is subjected to hydrophilic treatment, such as polyamide, polyester, and polyolefin. Moreover, the aggregates of the absorbent fibers have a shape with a thickness, such as a rectangle, circle, or polygon, due to stacking or interlacing multiple absorbent fibers. One type of aggregate having such a shape may be used alone or two or more types thereof may be used in combination.

(1-2) Water-Absorbent Resin

A known water-absorbent resin can be used as the water-absorbent resin. Specific examples of the water-absorbent resin include water-absorbent resins such as starch-acrylonitrile graft copolymer hydrolysates, substances obtained by neutralizing starch-acrylic acid graft polymers, saponified vinyl acetate-acrylic acid ester copolymers, and crosslinked partially neutralized acrylic acid polymers. Among these, from the industrial viewpoint such as supply capability and cost, crosslinked partially neutralized acrylic acid polymers are preferable. One type of water-absorbent resin may be used alone or two or more types thereof may be used in combination.

Examples of a method for manufacturing a crosslinked partially neutralized acrylic acid polymer include a reversed-phase suspension polymerization method and an aqueous solution polymerization method. Also, from the viewpoint of increasing the osmotic pressure and water-absorption capability of the water-absorbent resin, the degree of neutralization of the crosslinked partially neutralized acrylic acid polymer is preferably 50 mol % or more and more preferably 70 to 90 mol %. Also, in order to increase the absorption capability under the load, the vicinity of the surface of the water-absorbent resin that is used is preferably crosslinked.

From the viewpoint of providing flowability, a moisture ratio of the water-absorbent resin is preferably 20 mass % or less, and more preferably 10 mass % or less. Also, in order to increase the flowability, the water-absorbent resin may contain noncrystalline silica powder.

In general, the above-described water-absorbent resin is commercially available in a powder form, there is no particular limitation on the shape thereof, and examples of the shape include a spherical shape, an irregular crushed shape, a granular shape, a scaly shape, a short rod shape, and agglomerates thereof.

From the viewpoint of operability at the time of manufacture of the absorbent body, a medium particle size of the water-absorbent resin is preferably 200 to 600 μm, more preferably 250 to 500 μm, and even more preferably 300 to 450 μm. Note that in the present invention, the medium particle size of the water-absorbent resin is a value obtained using a measurement method below.

Measurement of Medium Particle Size 0.25 g of noncrystalline silica (Degussa Japan Co., Ltd., Siperant 200) is mixed into 50 g of water-absorbent resin powder as a lubricant. Next, JIS standard sieves are combined in the following order, starting from the top: a sieve having a sieve opening of 850 μm, a sieve having a sieve opening of 600 μm, a sieve having a sieve opening of 500 μm, a sieve having a sieve opening of 425 μm, a sieve having a sieve opening of 300 μm, a sieve having a sieve opening of 250 μm, a sieve having a sieve opening of 150 μm, and a saucer. Next, the mixture is introduced into the uppermost combined sieve, and is classified by shaking the sieves using a ro-tap shaker for 20 minutes. After classification, the masses of the mixture remaining on the sieves are calculated as mass percentages with respect to the total amount, the resulting values are integrated sequentially, starting from the largest particle size, and thereby the relationship between the sieve openings of the sieves and the value obtained by integrating the mass percentages of the mixtures remaining on the sieves is plotted on logarithmic probability paper. By connecting the plot on the probability paper with a straight line, a particle size corresponding to an integrated mass percentage of 50 mass % is denoted as the medium particle size.

There is no particular limitation on the content of the water-absorbent resin in the absorbent body, but from the viewpoint of obtaining a sufficient liquid absorption property also when the absorbent body according to the present invention is used in an absorbent article such as a diaper, the content of the water-absorbent resin is preferably 10 to 1000 g per square meter of the absorbent body (that is, 10 to 1000 $g/m^2$), more preferably 20 to 900 $g/m^2$, and even more preferably 30 to 700 $g/m^2$. From the viewpoint of achieving a sufficient liquid absorption property for the absorbent body and suppressing return of liquid in particular, this content is preferably 10 $g/m^2$ or more, and from the viewpoint of improving the permeability of liquid, this content is preferably 1000 $g/m^2$ or less.

The blending ratio of the water-absorbent resin in the absorbent body that can be produced in the present invention is preferably 5 to 90 mass %, more preferably 10 to 80 mass %, and even more preferably 15 to 70 mass %. When the blending ratio is less than 5 mass %, the amount of the water-absorbent resin is too small, which is not appropriate for an evaluation method. On the other hand, when the blending ratio exceeds 90 mass %, the absorbent fibers tend to separate from the absorbent body because the amount of the absorbent fibers is too small, which is not preferable.

(1-3) Size of Absorbent Body

There is no particular limitation on the size of an absorbent body that can be produced in the present invention, and when an absorbent body is evaluated as the absorbent body of a disposable diaper, the absorbent body may have a size of about 15 cm×10 cm to 80 cm×30 cm, for example, but the size thereof is not limited to this size.

(1-4) Modes of Material Body

The material body may have various modes.

(i) The water-absorbent resin is dispersively disposed on the upper surface of an aggregate of absorbent fibers.

(ii) The water-absorbent resin is dispersively disposed on a lower surface of an aggregate of the absorbent fibers.

(iii) The water-absorbent resin is dispersively disposed on the upper surface of an aggregate of the absorbent fibers, and an aggregate of the absorbent fibers is disposed thereon.

(iv) A plurality of (iii) are stacked. That is, the aggregates of the absorbent fibers and the water-absorbent resins are stacked alternately.

(v) A mixture of the aggregates of the absorbent fibers and the water-absorbent resin is used. This mixture can be obtained by purchasing a commercially available absorbent body or taking out an absorbent body from a commercially available disposable diaper. Alternatively, the mixture can be obtained by manufacturing an absorbent body using the manufacturing method of the present invention.

(vi) The water-absorbent resin is disposed on the upstream side (rear side in a conveying direction) of the aggregates of the absorbent fibers in a direction (the conveying direction) in which the material body is introduced into a gap, which will be described later, and is conveyed toward the gap using a conveying means such as a belt conveyor.

(vii) The water-absorbent resin is disposed on the downstream side (a front side in the conveying direction) of the aggregates of the absorbent fibers, and is conveyed toward the gap using a conveying means such as a belt conveyor.

In (i) to (v) above, the absorbent fibers and the water-absorbent resin are in contact with each other, and thus the absorbent fibers and the water-absorbent resin are simultaneously introduced into the gap, which will be described later, whereas in (vi) and (vii), the absorbent fibers and the water-absorbent resin are introduced into the gap at different times. That is, the absorbent resin is first introduced into the gap and then the absorbent resin is introduced, or the water-absorbent resin is first introduced into the gap and then the absorbent fibers are introduced into the gap. Also, it is possible to repeat (vi) and (vii) respectively, or combine (i) to (vii) as appropriate.

Also, according to (vi) above, a large amount of the water-absorbent resin can be dispersed on the upper portion of the absorbent body, and according to (vii), a large amount of the water-absorbent resin can be dispersed on the lower portion of the absorbent body. Also, according to (v) above, it is possible to change the mixing ratio or mixed state of the absorbent fibers and the water-absorbent resin in the absorbent body that has already been produced.

2. Method for Manufacturing Absorbent Body

The absorbent body is manufactured in steps below.

(2-1) First Step

First, the above-described material body is prepared. The material body may have various modes as described above. This material body is successively introduced into a gap that is smaller than its thickness. The gap is formed by two surfaces, namely, the first surface and the second surface, and recesses and protrusions are formed on at least one of the surfaces.

The material body can be introduced into the gap using various methods. For example, the material body can be successively introduced into the gap by manually pushing the material body little by little or using a conveying means such as a belt conveyor. Also, the gap is smaller than the thickness of the material body, and thus the material body can also be introduced into the gap while the material body is pressed in the thickness direction.

The first surface and the second surface can have various modes. For example, a surface of a pair of plate materials that face each other and are parallel to each other or curve may be denoted as the first surface and the second surface, or an outer circumferential surface of the cylindrical body may be denoted as the first surface and an arc-shaped second surface can be formed so as to face the first surface. Also, at least one of the first surface and the second surface is configured to move in parallel. For example, when the first surface is formed on the outer circumferential surface of the cylindrical body, the cylindrical body is constituted to be rotatable.

Also, recesses and protrusions are formed on at least one of the first surface and the second surface. For example, recesses and protrusions may be formed on the entire first surface, and no recesses or protrusions may be formed on the second surface. Alternatively, recesses and protrusions can also be formed on a portion of the second surface or the entire second surface. When recesses and protrusions are formed on a portion of the second surface, for example, as described later, recesses and protrusions can be formed on the second surface on the downstream side in the direction in which the material body moves.

Recesses and protrusions can have various modes. For example, recesses and protrusions can be formed by forming the second surface using a plate material and forming a through hole in this plate material. Also, in particular, as described later, such a through hole can be provided in a portion of the second surface on the downstream side in the direction in which the material body moves. A mesh plate material made of metal or the like can be adopted as a member that constitutes such a second surface, for example.

(2-2) Second Step

In the second step, the absorbent fibers and the water-absorbent resin of the material body are mixed. That is, after the material body is introduced into the gap, a shearing force is applied to the material body by moving the second surface relative to and parallel to the first surface, and the absorbent fibers and the water-absorbent resin are mixed. Since recesses and protrusions are formed on at least one of the first surface and the second surface, a shearing force is applied to the material body that was introduced into the gap due to the recesses and protrusions by moving these surfaces relative to and parallel to each other. In particular, if recesses and protrusions are formed on both the first surface and the second surface, a strong shearing force is applied to the material body, and thus mixing is facilitated. Also, when the material body is introduced into the gap using a belt conveyor, the first surface or the second surface is moved relative to the other at a speed that is higher than a conveying speed of the belt conveyor.

When the first surface is moved relative to the second surface at a high speed, the material body can be moved along the gap. In this case, as described above, if recesses and protrusions are formed on the second surface on the downstream side in the direction in which the material body moves, the shearing force increases along with the movement of the material body, and mixing is facilitated along with the movement. Moreover, when a through hole is formed on the downstream side of the second surface and the second surface is disposed on the lower side of the first surface, the mixed absorbent fiber and water-absorbent resin fall via the through hole, and thus, it is possible to smoothly move to a third step that will be described below.

(2-3) Third Step

In the third step, the mixed absorbent fibers and the water-absorbent resin are caused to fall and are stacked by suctioning the absorbent fibers and the water-absorbent resin in a recessed portion having a predetermined shape. The mixed absorbent fiber and water-absorbent resin are preferably caused to fall in a closed space, for example. Moreover, if a recessed portion is disposed at a lower end of the closed space, it is possible to uniformly stack the absorbent fibers and the water-absorbent resin.

Although there is no particular limitation on the shape of the closed space, the closed space may increase in size toward its lower end, and the recessed portion can correspond to the shape of the lower end of the closed space.

The recessed portion can have various shapes and the shape thereof can be determined in accordance with the shape of the desired absorbent body. Also, the absorbent fibers and the water-absorbent resin can be uniformly stacked in the recessed portion by disposing a breathable bottom plate in the recessed portion and performing suction via this bottom plate. Suction can be performed using a suction apparatus such as a known vacuum cleaner or a vacuum pump, for example, but there is no limitation thereto.

3. Apparatus for Manufacturing Absorbent Body

Figure 1:
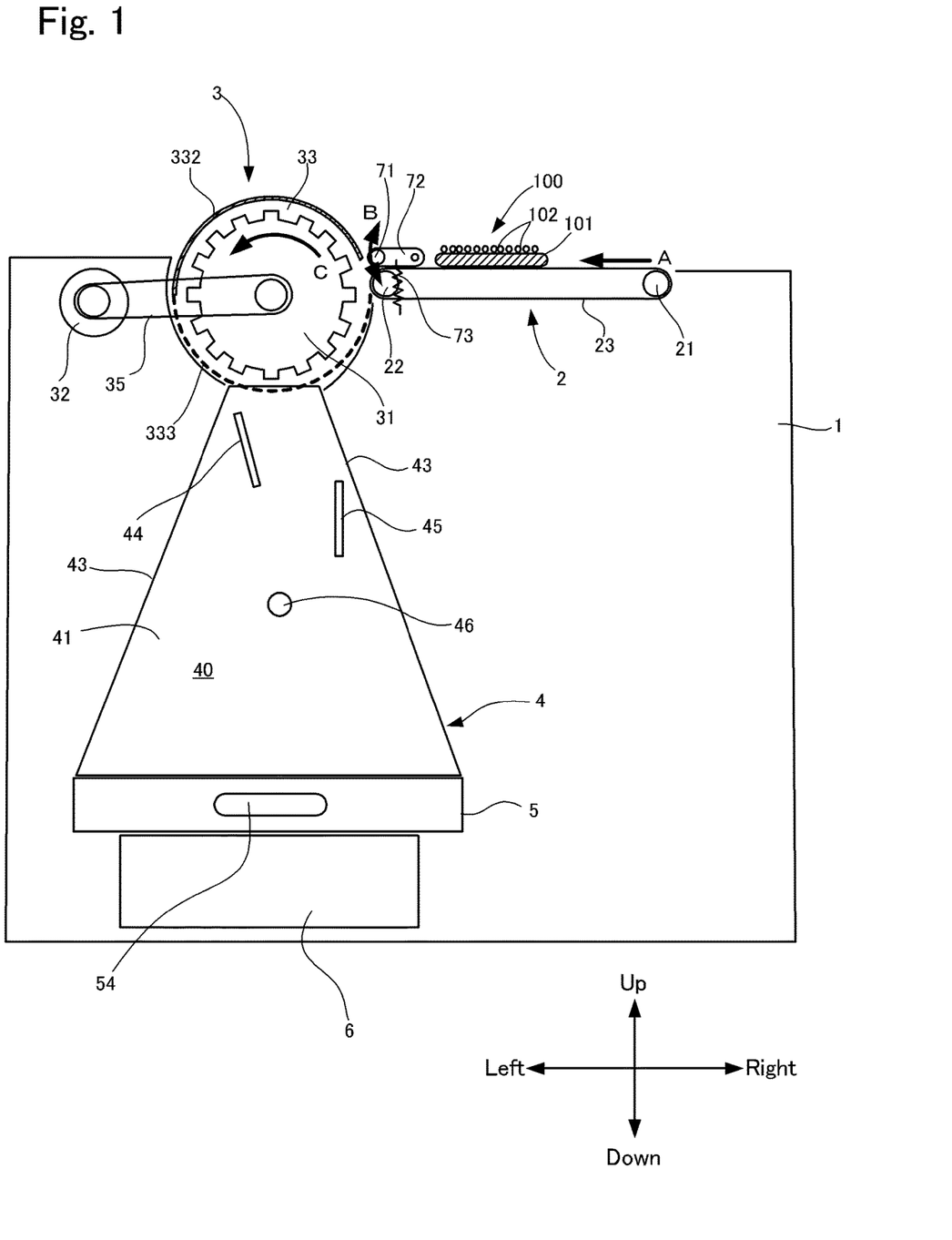
FIG. 1 is a front view showing a schematic configuration of one embodiment of a manufacturing apparatus according to the present invention.
Figure 2:
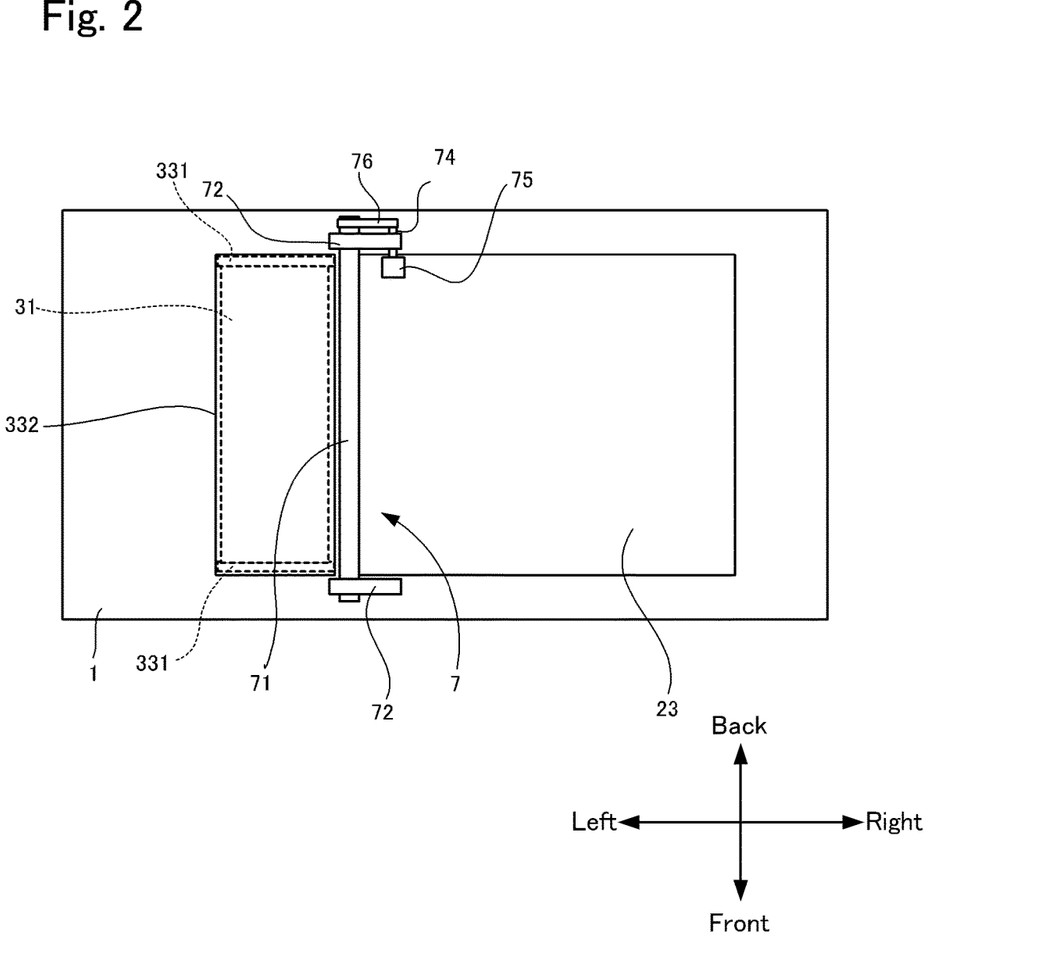
FIG. 2 is a plan view of FIG. 1.

Next, one example of the manufacturing apparatus that realizes the method for manufacturing an absorbent body as described above will be described with reference to the drawings. FIG. 1 is a front view showing a schematic configuration of this manufacturing apparatus, and FIG. 2 is a plan view of FIG. 1. Hereinafter, for convenience, description will be given with reference to the orientation shown in FIGS. 1 and 2, but the apparatus according to the present invention is not limited by this orientation.

As shown in FIGS. 1 and 2, this manufacturing apparatus includes a rectangular parallelepiped housing 1, and this housing 1 is provided with a conveying unit 2 that conveys a material body 100, a mixing unit 3 that mixes absorbent fibers and a water-absorbent resin of the material body 100, a chamber portion 4 having an internal space 40 through which the mixed absorbent fibers and the water-absorbent resin fall, a stacking portion 5 in which the absorbent fibers and the water-absorbent resin that have fallen are stacked, and a suction unit 6 that suctions air in the internal space 40 in the chamber portion 4. Hereinafter, each part will be described in detail.

First, the conveying unit 2 will be described. The conveying unit 2 is provided on the upper surface of the housing 1, and is constituted by a belt conveyor disposed on the right side of the upper surface of the housing 1. That is, the conveying unit 2 includes a driven roller 21 that is disposed on the right side of the upper surface of the housing and extends in the front-back direction, a driving roller 22 that extends in the front-back direction near the center of the upper surface of the housing, and a conveying belt 23 that is bridged over these rollers 21 and 22, and the driving roller is rotationally driven by a first motor (not shown). With this configuration, the material body 100 disposed on the conveying belt 23 moves leftward (see arrow A in FIG. 1). Also, as described later, this conveying unit 2 is provided with a guide portion 7 that guides the material body 100 conveyed by the conveying belt 23 to the mixing unit 3. Note that the speed of the conveying belt 23 is 0.1 to 20.0 mm/sec, for example.

Next, the mixing unit 3 will be described. The mixing unit 3 includes a cylindrical body 31 that is disposed on the left side of an upper end portion of the housing 1 and is rotatably supported by the housing 1, a second motor (driving portion) 32 that drives this cylindrical body 31, and a gap formation portion 33 for forming a gap between the gap formation portion and an outer circumferential surface of the cylindrical body 31 through which the material body 100 passes. The cylindrical body 31 has a surface on which recesses and protrusions are formed, and rotates about a rotation axis extending in the front-back direction. Moreover, the outer circumferential surface of the cylindrical body 31 and a left end portion of the above-described conveying unit 2 are close to each other. Therefore, the material body 100 conveyed leftward on the conveying unit 2 is guided to the outer circumferential surface of the cylindrical body 31 by the guide portion 7, which will be described next.

The guide portion 7 includes a rod-shaped pressing member 71 having a circular cross section that presses the material body 100. This pressing member 71 extends in the front-back direction so as to pass over the left end portion of the conveying unit 2. Rod-shaped support members 72 are attached to two ends of the rotatable pressing member 71. The support members 72 extend in a direction orthogonal to the pressing member 71 and are disposed to hold the conveying belt 23. Moreover, tips of the support members 72 are rotatably attached to the upper surface of the housing 1. Accordingly, the pressing member 71 freely swings centered on the tips of the support members 72 (see arrow B in FIG. 1). Also, a gap is formed between the pressing member 71 and the conveying belt 23, and the material body 100 passes through this gap. This gap is smaller than the thickness of the material body, and may be about 0 to 50 mm, for example, in accordance with the thickness of the material body.

Spring members 73 are attached between the two ends of the pressing member 71 and the upper surface of the housing 1, and the pressing member 71 is biased downward by these spring members 73. That is, when the material body 100 having a larger thickness than the gap between the pressing member 71 and the conveying belt 23 passes therethrough, the pressing member 71 is pushed upward against the spring members 73 and the material body 100 passes therethrough. However, the thickness of the material body 100 that is introduced into the mixing unit 3 is made as small as possible by preventing the pressing member 71 from being pushed upward by the spring members 73 as much as possible.

Furthermore, a support axis 74 is inserted so as to pass through, in the front-back direction, the tip of the support member 72 that is disposed rearward, and a roller 75 that is rotated by the conveying belt 23 is attached to a front end of this support axis 74. This roller 75 rotates together with the support axis 74 along with the movement of the conveying belt 23 due to friction with the conveying belt 23. On the other hand, a belt 76 is bridged between a rear end of the support axis 74 and a rear end in the axial direction of the pressing member 71, and when the support axis 74 rotates, the pressing member 71 also rotates. Therefore, the pressing member 71 is configured to rotate in synchronization with the movement of the conveying belt 23, and accordingly, the material body 100 is pushed toward the mixing unit 3 by rotation of the pressing member 71.

The description of the mixing unit 3 will continue. The above-described second motor 32 is disposed on the left side of the cylindrical body 31, a belt 35 is bridged over a rotation axis of this second motor 32 and the rotation axis of the cylindrical body 31, and the cylindrical body 31 is rotated leftward by belt transmission (see arrow C in FIG. 1). The rotation speed of the cylindrical body 31 may be 1000 to 5000 r/min, for example.

Next, the gap formation portion 33 will be described. The gap formation portion 33 includes a pair of circular frames 331 that are disposed outward from both sides of the cylindrical body 31 and whose outer diameter is slightly larger than that of the cylindrical body 31. Moreover, a cover member 332 having an arc shaped cross section and a mesh member (plate-shaped member) 333 are detachably attached to the outer circumferential surfaces of these frames 331 so as to cover the cylindrical body 31. The cover member 332 is formed by a cross-sectionally arc-shaped plate member that passes over the cylindrical body 31 near the pressing member 71 and extends toward the left end of the cylindrical body 31. Also, the mesh member 333 is a thin mesh plate member that is made of metal or the like and is provided with multiple small holes, and has an arc shape so as to pass below the cylindrical body 31 from the left end of the cover member 332 and extends to the vicinity of the conveying unit.

As described above, the frames 331 are slightly larger than the outer diameter of the cylindrical body 31, and thus gaps are formed between the cover member 332 attached on these frames 331, the mesh member 333, and the outer circumferential surface of the cylindrical body 31, and the material body 100 passes through these gaps. However, it is preferable to make the gap between the mesh member 333 and the cylindrical body 31 smaller than the gap between the cover member 332 and the cylindrical body 31 by adjusting the frames, and the gap between the cover member 332 and the cylindrical body 31 may be 2 mm, and the gap between the mesh member 333 and the cylindrical body 31 may be 1 mm, for example.

Next, the chamber portion 4 will be described. The chamber portion 4 is constituted by a front panel 41 having a trapezoidal shape in front view, a rear panel (not shown), and a pair of side panels 43 that connect inclined sides to each other on both sides of these front panel 41 and rear panel, and the chamber portion 4 has the internal space 40 surrounded by these panels. An upper end and a lower end of this internal space 40 are open, and the width of the inner portion gradually increases in the horizontal direction as its lower side is approached. An upper end opening of the internal space 40 is disposed directly below the cylindrical body 31, and gaps around the cylindrical body 31 and the internal space 40 communicate with each other via the mesh member 333.

Furthermore, a plurality of guide members are disposed in the internal space 40. Although the guide members can have various configurations, three guide members are provided in the present embodiment. That is, a first plate-shaped guide member 44 disposed near the upper end of the internal space 40 on the left side and a second plate-shaped guide member 45 that is disposed slightly below the first guide member 44 on the right side of the internal space 40 are provided, and a rod-shaped third guide member 46 that extends in the front-back direction is provided near the center of the internal space 40. These three guide members 44 to 46 extend in the front-back direction so as to connect the front panel 41 and the rear panel (not shown).

The first guide member 44 extends downward and guides the mixed absorbent fibers and water-absorbent resin rightward in order to prevent the mixed absorbent fibers and water-absorbent resin from moving excessively leftward in the internal space 40. The second guide member 45 extends downward and guides the absorbent fibers and the water-absorbent resin leftward such that the absorbent fibers and the water-absorbent resin that are guided rightward by the first guide member 44 do not move excessively to a right end of the internal space 40. Also, the third guide member 46 guides the absorbent fibers and the water-absorbent resin that fall such that in particular, the water-absorbent resin falls uniformly to the left and the right of the internal space 40.

Figure 3:
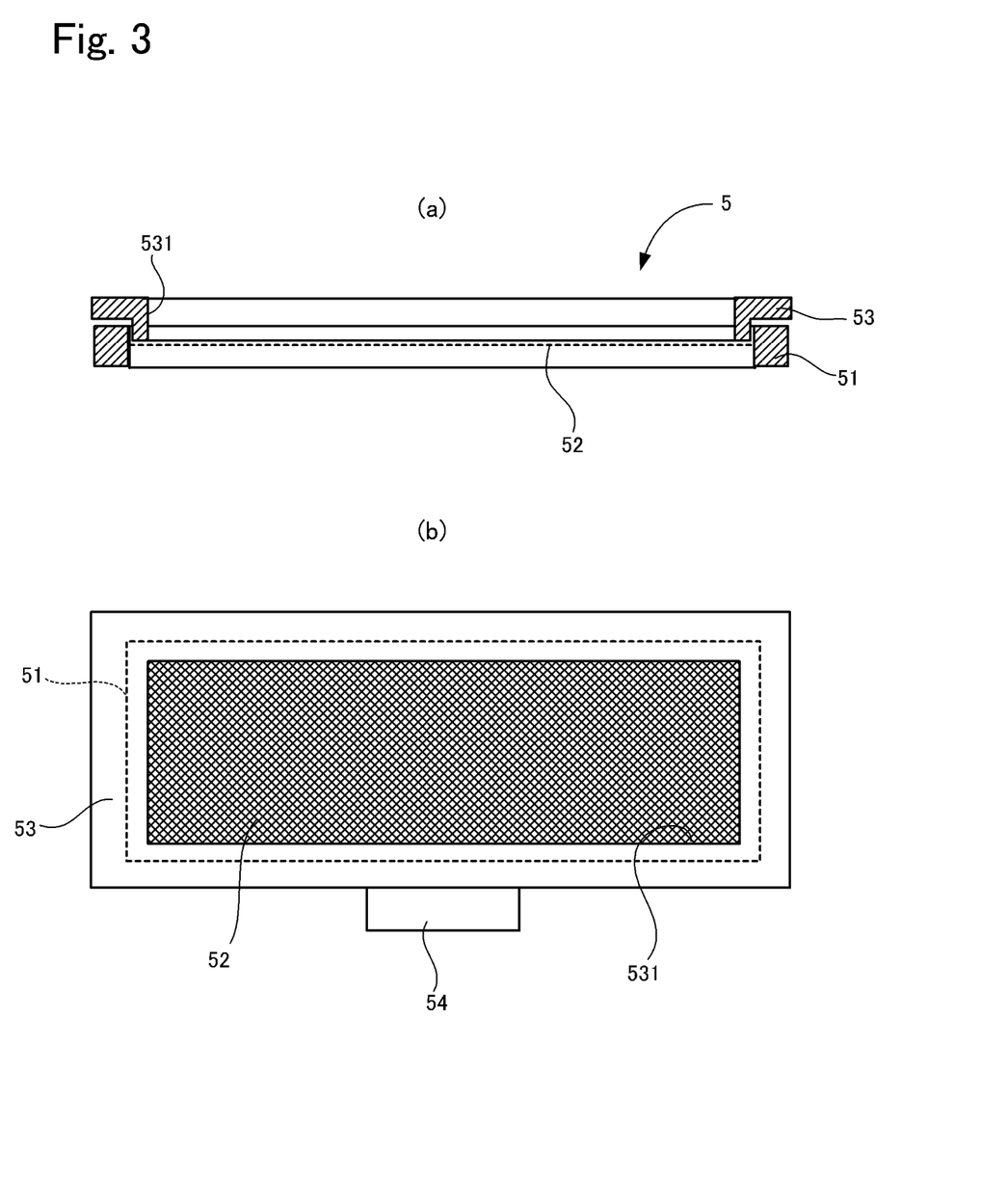
FIG. 3 is a cross-sectional view (a) and a plan view (b) of a stacking portion.

Next, the stacking portion 5 will be described with reference to FIG. 3. The stacking portion 5 is disposed below the chamber portion 4 so as to cover the lower end opening of the chamber portion 4, and is a site on which the absorbent fibers and the water-absorbent resin that have fallen are stacked. Specifically, as shown in FIG. 3, the stacking portion 5 includes a rectangular support frame 51 having a size similar to that of the lower end opening of the chamber portion 4, a plate-shaped mesh air circulation member 52 that is fitted to this support frame 51 and provided with multiple small holes, and a frame member 53 having a frame shape disposed detachably from this air circulation member 52, and the absorbent fibers and the water-absorbent resin are stacked in a recessed portion 531 surrounded by the frame member 53. That is, a desired absorbent body is formed depending on the shape of the frame member 53. Moreover, this stacking portion 5 can be drawn frontward below the chamber portion 4. That is, a handle 54 is attached to a front portion of the support frame 51, and the stacking portion 5 can be removed from the housing 1 by pulling this handle 54. Note that the handle 54 preferably has a detachable structure such that the back and the front in the direction in which the stacking portion 5 is inserted can be reversed.

The suction unit 6 is disposed below this stacking portion 5. The suction unit 6 is constituted by a suction opening through which the stacking portion 5 is suctioned from below and a suction apparatus such as a known cleaner or a vacuum pump, and suctions the air in the internal space 40 in the chamber portion 4 downward. That is, the air in the internal space 40 is suctioned downward via the air circulation member 52 of the stacking portion 5. The negative pressure caused by this suction can be monitored by installing a differential pressure gauge in the chamber portion, and an absorbent body can be produced under a constant negative pressure condition by installing a valve for pressure adjustment in the suction unit 6.

The sizes of the above-described conveying unit 2, mixing unit 3, chamber portion 4, stacking portion 5, and suction unit 6 are adjusted in accordance with the size of an absorbent body for evaluation that is to be produced, and an absorbent body that has uniform distribution of the absorbent fibers and the water-absorbent resin can be produced in the plane direction. The size of the absorbent body that can be produced is determined by the size of the recessed portion 531 of the stacking portion 5, and the size of the absorbent body is preferably in a range of 15 cm×10 cm to 80 cm×30 cm, and more preferably in a range of 20 cm×10 cm to 60 cm×20 cm. An absorbent body having a size of 15 cm×10 cm or less is too small to serve as the absorbent body for evaluation, the amount of liquid that can not be absorbed and leaks becomes too high, and a difference in evaluation is unlikely to occur, and there is no demand for it to be used in a testing method. Moreover, if an absorbent body having a size of 80 cm×30 cm or more is used, it is difficult to uniformly distribute such an absorbent body in the short axis direction of the absorbent body due to the mechanism of the apparatus, and thus such an absorbent body is not preferable as the absorbent body for evaluation.

Note that it is preferable that a breathable sheet member such as tissue paper is disposed on the above-described air circulation member 52, and the absorbent body is stacked thereon.

4. Operation of Manufacturing Apparatus

Next, operations of the manufacturing apparatus that has been constituted as described above will be described. First, a highly breathable sheet member (for example, tissue or nonwoven fabric) (not shown) is disposed on the air circulation member 52 of the stacking portion 5. This is for preventing the stacked absorbent fibers and water-absorbent resin from coming off of pores of the air circulation member 52. Note that when the power source of the suction apparatus is turned on, it is confirmed that the above-described sheet member is not misaligned. Next, a material body 100 is prepared. As described above, the material body 100 has various modes, but as shown in FIG. 1 as one example, an aggregate 101 of the absorbent fibers formed into an approximately rectangular shape is disposed on the conveying belt 23 of the conveying unit 2, and a water-absorbent resin 102 is dispersively disposed thereon uniformly to the left and the right with respect to the direction in which the belt advances. However, the aggregate 101 of the absorbent fibers may have various shapes other than an approximately rectangular shape as described above.

Next, after the second motor 32 and the suction apparatus are driven, the first motor is driven. Accordingly, the material body 100 on the conveying belt 23 moves leftward and is guided to the mixing unit 3 while being pressed by the pressing member 71. Because the cylindrical body 31 of the mixing unit 3 rotates at a high speed, the material body 100 introduced into the mixing unit 3 enters the gap while being cut off in sequence. At this time, the material body 100 moves counterclockwise in the gap due to rotation of the cylindrical body 31. Also, recesses and protrusions are formed on the outer circumferential surface of the cylindrical body 31, and thus crushed absorbent fibers and water-absorbent resin are mixed while the material body 100 is rubbed between the cover member 332 and the cylindrical body 31. Then, the material body 100 is further rubbed between the mesh member 333 and the cylindrical body 31 after passing through the cover member 332. That is, the material body 100 is crushed due to shearing between the recesses and protrusions of the cylindrical body 31 and the recesses and protrusions of the mesh member 333, and the absorbent fibers and the water-absorbent resin are further mixed. Upon reaching the lower portion of the cylindrical body 31, the absorbent fibers and the water-absorbent resin that were mixed fall downward from the pores of the mesh member 333, assisted by suction performed by the suction unit 6. Note that the absorbent fibers and the water-absorbent resin that do not fall here are mixed while further moving through the gap and being rubbed by the cylindrical body 31 and eventually fall from the mesh member 333.

Then, the absorbent fibers and the water-absorbent resin that fell from the mesh member 333 are stacked in the recessed portion 531 formed by the frame member 53 of the stacking portion 5 while falling through the internal space 40 of the chamber portion 4. In the process in which the absorbent fibers and the water-absorbent resin fall, the absorbent fibers and the water-absorbent resin are uniformly stacked in the recessed portion 531 by the above-described three guide members 44 to 46.

In this manner, the absorbent fibers and the water-absorbent resin are mixed in the recessed portion 531, and an absorbent body stacked in a predetermined weight per area is formed. Thereafter, after the motors and the suction apparatus are turned off, when the stacking portion 5 is drawn to the front, the absorbent body can be removed from the apparatus.

5. Features

As described above, according to the above-described apparatus, the material body 100 is gradually introduced into the mixing unit having the cylindrical body 31 that rotates at a high speed, and thus the material body 100 is cut off little by little and introduced into the gap due to the rotation of the cylindrical body 3*l*. Then, the material body 100 introduced in the gap is rubbed between the cylindrical body 31 having recesses and protrusions and the cover member 332 and between the cylindrical body 31 and the mesh member 333, and is mixed while receiving a shearing force. Thereafter, the absorbent fibers and the water-absorbent resin that were mixed fall and are stacked uniformly in the recessed portion 531. As a result, it is possible to obtain an absorbent body in which the absorbent fibers and the water-absorbent resin are mixed uniformly and have a uniform thickness. Therefore, similarly to a commercial production line, the apparatus for manufacturing an absorbent body according to the present embodiment, which is a small apparatus, can manufacture an absorbent body in which the absorbent fibers and the water-absorbent resin are uniformly mixed. That is, an absorbent body can be easily manufactured similarly to a commercial production line without using a commercial production line, and thus various types of testing of a water absorption property or the like can be performed using the absorbent body according to the present embodiment.

Also, the material body 100 is mainly manually produced, and at this time, the blending amount of the absorbent fibers and the water-absorbent resin can be modified as appropriate, and even though such modification is made, a uniformly mixed absorbent body can be manufactured using the above-described apparatus. Thus, the blending amount of the absorbent fibers and the water-absorbent resin can be easily changed in accordance with the evaluation content, and thus an absorbent body for testing having a desired formulation can be easily manufactured.

6. Variation

Although the embodiment of the present invention was described above, the present invention is not limited to the above-described embodiment, and various modifications can be made without departing from the gist of the present invention. Note that variations below can be combined as appropriate.

(6-1)

There is no particular limitation on the length of the mesh member 333 in the circumferential direction of the cylindrical body 31, and the mesh member 333 needs only to be disposed to cover the upper opening of the chamber portion 4 so as to connect at least the chamber portion 4 and the gap. However, when the mesh member 333 extends longer toward the downstream side than the upper opening of the chamber portion 4, the shearing effect with the cylindrical body 31 increases, which can further facilitate mixing of the absorbent fibers and the water-absorbent resin.

Also, in the above-described embodiment, the mesh member 333 has the role of applying a shearing force to the material body 100 between the cylindrical body 31 and the mesh member 333, and the role of connecting the gap and the chamber portion 4, but these roles can be separated from each other. That is, a member (a mixing portion) provided with recesses and protrusions that can apply a shearing force to the material body 100 between the cylindrical body 31 and the mixing portion may be disposed, and a member (a connection portion) that connects the gap and the chamber portion 4 may also be disposed separately from the mixing portion. Also, the recesses and protrusions may be formed in the cover member 332.

Also, in the above-described embodiment, in the gap through which the material body 100 passes, first, the material body 100 passes between the cover member 332 and the cylindrical body 31, then, the material body 100 passes between the mesh member 333 and the cylindrical body 31, and the absorbent fibers and the water-absorbent resin fall from through holes on the downstream side of the mesh member 333. That is, the material body 100 passes through the gap in which recesses and protrusions are provided on one surface and then passes through the gap in which recesses and protrusions are provided on both surfaces, and thereafter, the absorbent fibers and the water-absorbent resin fall. There is no particular limitation on the configuration of such a gap, and recesses and protrusions may be formed on both surfaces, across the entire gap. Also, it is possible to change positions as appropriate, such as the material body first passing through a site at which recesses and protrusions are formed on both surfaces, or mixing sites at which recesses and protrusions are formed on both surfaces and sites at which recesses and protrusions are formed on one surface.

(6-2)

Although there is no particular limitation on the shape of the chamber portion 4, when the shape of the absorbent body 10 that is manufactured is larger than the upper opening of the chamber portion 4, the chamber portion 4 has a shape that widens toward the bottom as described above. Also, the guide members 44 to 46 of the chamber portion 4 need only to be provided as needed such that the absorbent fibers and the water-absorbent resin are uniformly stacked, and are not necessarily required. Also, the number and the shape of guide members can be changed as appropriate.

(6-3)

There is no particular limitation on the configuration of the conveying unit 2, and the conveying unit 2 may have a configuration other than the belt conveyor as described above and need only to guide the material body 100 to the mixing unit 3.

Working Example

Hereinafter, working examples of the present invention will be described. However, the present invention is not limited to the working examples below.

A. Specification of Manufacturing Apparatus

First, the manufacturing apparatus described in the above-described embodiment was prepared as a working example. A specific specification is as follows.

(1) Conveying Unit

| (i) Conveying speed | 1.6 (mm/sec) |
|---|---|

(2) Cylindrical Body

| (i) Size | φ70 mm × 200 mm |
|---|---|
| (ii) Rotation speed | 2700 rotations/min |
| (iii) Height of protrusions | 4 mm |

(3) Gap Formation Portion

| (i) Gap between cover member and cylindrical body | 2 mm |
|---|---|
| (ii) Gap between mesh member and cylindrical body | 1 mm |
| (iii) Position of mesh member | Below cylindrical body over central angle of approximately 90 degrees |

(4) Chamber Portion

| (i) Opening width of upper end | 63 mm |
|---|---|
| (ii) Opening width of lower end | 380 mm |
| (iii) Height | 440 mm |

(5) Stacking Portion
  (i) Size of recessed portion in frame member
  width 120 mm×length 400 mm
(6) Suction Portion
  (i) A Vacuum Cleaner that Operates at 100 V was Used as the Suction Apparatus B. Manufacture of Absorbent Body First, the apparatus was prepared by placing tissue paper (width 140×length 420 mm) having a basis weight of 16 g/m² on the stacking portion, such that absorbent fibers and water-absorbent resin were stacked thereon. Next, 10 g of absorbent fibers were molded as an aggregate having a shape with a width of 125 and a length of 450 mm, and 10 g of water-absorbent resin was uniformly dispersed manually thereon to form a material body. Leif lock produced by Leonia Co., Ltd. was used as the absorbent fibers and AQUA KEEP SA55SXII produced by SUMITOMO SEIKA CHEMICALS CO., LTD. was used as the water-absorbent resin. Next, that material body was disposed on the conveying unit of the above-described manufacturing apparatus, and all of the motors and the suction apparatus were driven. The entire material body was introduced into the mixing unit, and thereafter, when the absorbent fibers and the water-absorbent resin that were mixed were stacked in the stacking portion, an absorbent body shown in FIG. 4 was obtained.

C. Evaluation of Absorbent Body

1. Evaluation of External Appearance

Figure 4:
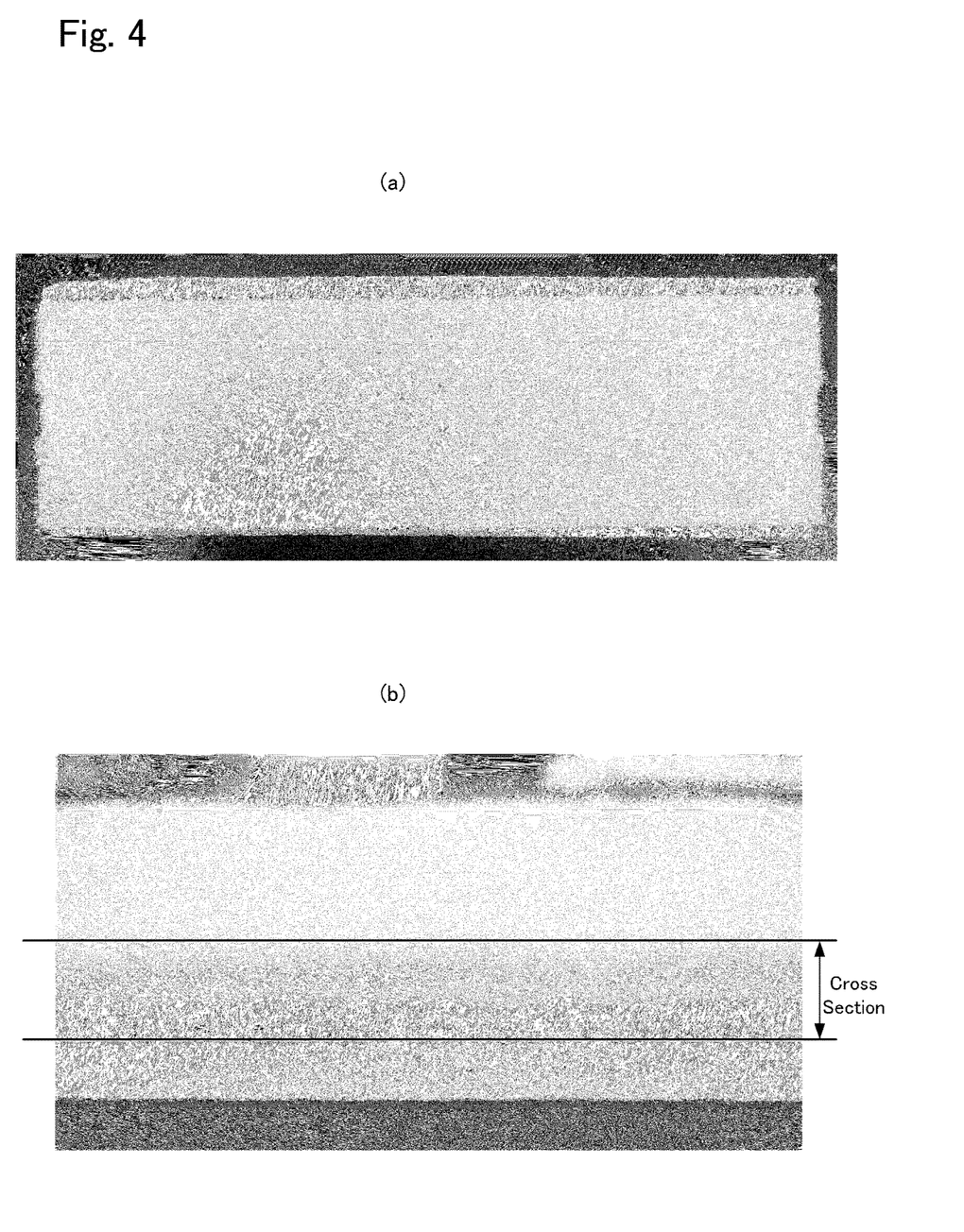
FIG. 4 is a plan view (a) and a partial front view (b) of an absorbent body obtained using a manufacturing apparatus according to a working example.

The external appearance was evaluated using an absorbent body obtained by using a water-absorbent resin that was colored red in advance so as to be easily visually recognizable in the manufacture of the above-described absorbent body. As shown in FIG. 4, it is found that the absorbent fibers and the water-absorbent resin are uniformly mixed in that absorbent body (white portions in FIG. 4 indicate absorbent fibers and grey portions indicate water-absorbent resin). That is, as shown in FIG. 4(a), the water-absorbent resin is uniformly distributed in the plane direction, and as shown in FIG. 4(b), it is uniformly distributed in the thickness direction as well.

2. Evaluation of Distribution State of Absorbent Fibers and Water-Absorbent Resin Using Water Absorption Test (2-1) Water Absorption Test of the Absorbent Body was Conducted in Accordance with Procedures Below.

Figure 5:
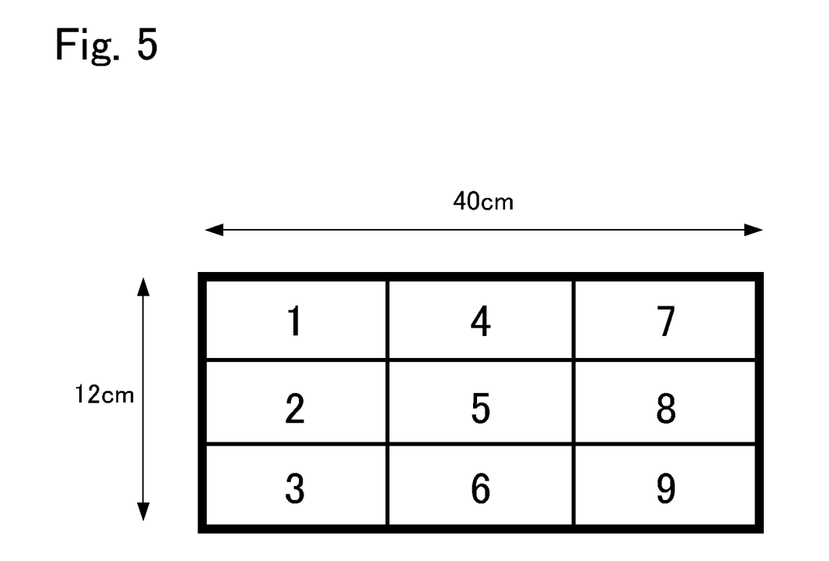
FIG. 5 is a plan view showing division of the absorbent body when absorbent pieces are produced.

(i) As shown in FIG. 5, the obtained absorbent body was divided into three in the longitudinal direction and the lateral direction, that is, it was divided into nine to produce absorbent pieces, and a weight C (g) of each piece was measured.

(ii) The absorbent pieces were immersed in 8 L of an ion exchange water, and left for 30 minutes. (The ion exchange water was stirred for 10 seconds immediately after the immersion so as to spread the pieces.)

(iii) The absorbent pieces that were spread in the ion exchange water were filtered using a standard sieve (having a diameter of 20 cm and a sieve opening of 75 μm) that was weighted in advance, and water was drained with the standard sieve tilted for 30 minutes.

(iv) The weight of the absorbent pieces together with the standard sieve was measured, and a weight D (g) of the absorbent pieces that absorbed water was obtained.

(v) The content of the water-absorbent resin in each absorbent piece was calculated using the following equations using anion exchange water absorption capacity A (g/g) of the water-absorbent resin and an ion exchange water absorption capacity B (g/g) of the absorbent fibers that were calculated as shown in (2-2) and (2-3) below.

When the weight of the water-absorbent resin is X (g) and the weight of the absorbent fibers is Y (g), Equations (1) and (2) below are true.

$$X+Y=C \quad (1)$$

$$AX+BY=D \quad (2)$$

X and Y can be calculated using these Equations (1) and (2) as described below.

$$X=(D-BC)/(A-B)$$

$$Y=C-X$$

(2-2) Ion Exchange Water Absorption Capacity (g/g) of Water-Absorbent Resin (i) 1000 ml of the ion exchange water was introduced into a beaker.

(ii) 0.5 g of the water-absorbent resin were added to the ion exchange water in the beaker and left for 30 minutes.

(iii) The water-absorbent resin that absorbed water was transferred to a standard sieve that was weighted in advance, and water was drained with the standard sieve tilted for 30 minutes.

(iv) The weight (m) of the water-absorbent resin on the standard sieve was measured, and the ion exchange water absorption capacity A (g/g) of the water-absorbent resin was obtained using Equation (3) below.

$$A\ (g/g)=m\ (g)/0.5\ (g) \quad (3)$$

(2-3) Ion Exchange Water Absorption Capacity (g/g) of Absorbent Fibers (i) 1000 ml of the ion exchange water was introduced into a beaker.

(ii) 1.0 g of the absorbent fibers was added to the ion exchange water in the beaker.

(iii) The beaker was left for 30 minutes.

(iv) The absorbent fibers that absorbed water were transferred to a standard sieve that was weighted in advance, and water was drained with the standard sieve tilted for 30 minutes.

(v) The weight (m) of the absorbent fibers on the standard sieve was measured, and the measured weight (m) was denoted as the ion exchange water absorption capacity B (g/g) of the absorbent fibers.

3. Result of Water Absorption Test

First, two absorbent bodies (Samples No. 1 and 2) were manufactured using the manufacturing apparatus according to the working example, and the total weight (g) of each absorbent body was measured. Separately, the ion exchange water absorption capacity A of the water-absorbent resin that was used to produce the absorbent bodies and the ion exchange water absorption capacity B (g/g) of the absorbent fibers that was used to produce the absorbent bodies were measured and calculated. The results are as shown below.

The ion exchange water absorption capacity A of the water-absorbent resin=355.3 (g/g)

The ion exchange water absorption capacity B of the absorbent fibers=15.0 (g/g)

The total weight of Sample No. 1 absorbent body=19.85 (g)

The total weight of Sample No. 2 absorbent body=19.67 (g)

Figure 6:
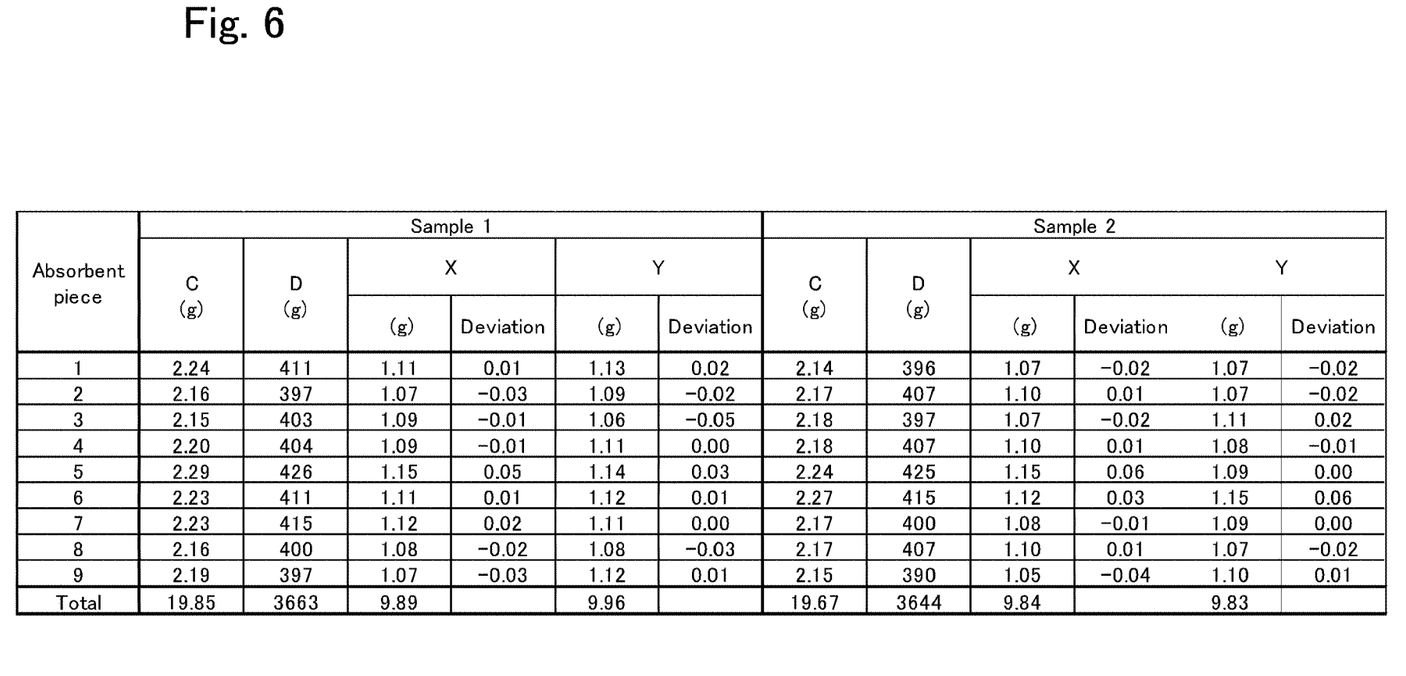
FIG. 6 is a table showing the water-absorption properties of absorbent bodies manufactured using the manufacturing apparatus according to a working example.

Then, the content of the absorbent fibers and the content of the water-absorbent resin of each absorbent piece obtained from each sample were calculated using A, B, and C, which were measured before the water absorption test, and D, which was obtained by water absorption test. Also, the average value of the absorbent fiber amounts and the water-absorbent resin amounts that were obtained using the absorbent pieces obtained from the samples was obtained, and deviations from the average value were also obtained. The results are as shown in FIG. 6. According to FIG. 6, it is found that in all of the samples, the nine absorbent pieces had approximately the same amount of the absorbent fibers and the water-absorbent resin. Therefore, it was found that use of the manufacturing apparatus according to the present working example made it possible to manufacture an absorbent body in which the absorbent fibers and the water-absorbent resin were approximately uniformly dispersed in the plane direction. In general, the dispersiveness of the water-absorbent resin in the long axis direction is unlikely to be uniform, but it was found that as described above, use of the manufacturing apparatus according to the present working example made it possible to make the dispersiveness in both directions, that is, in the long axis direction and the short axis direction, approximately the same.

Also, if the manufacturing apparatus according to the present working example is used, the absorbent body can be manufactured using about 10 g of the water-absorbent resin, and the water-absorbent resin can be evaluated in the state of the absorbent body. That is, even if the amount of the water-absorbent resin is not sufficient to be used in manufacture in an actual plant, if there are several tens of grams of the water-absorbent resin or several hundreds of grams of the water-absorbent resin that can be manufactured in the laboratory, use of the manufacturing apparatus according to the present working example makes it possible to evaluate the water-absorbent resin as the absorbent body.

Note that examples of evaluation on the absorbent body include items below.
a) Speed at which a predetermined amount of artificial urine is absorbed by the absorbent body (permeation time)
b) Return amount that occurs when a load is applied to the absorbent body that absorbed liquid (return amount)
c) Area of poured artificial urine spreading in the absorbent body (diffusion length)
d) Amount of liquid that leaks from the absorbent body when a predetermined amount of artificial urine is poured to the absorbent body (amount of liquid that leaks)
e) Amount of artificial urine that can be absorbed by the entire absorbent body (absorption capacity)

D. Measurement of Property of Absorbent Body in which Water-Absorbent Resin is Used Next, an evaluation test of the absorbent body produced in the above-described working example was performed.

Specifically, the evaluation test shown below was performed using artificial urine.

1. Preparation of Artificial Urine

An appropriate amount of distilled water was introduced into a 10 L container, and 60 g of sodium chloride, 1.8 g of calcium chloride dihydrate, and 3.6 g of magnesium chloride hexahydrate were added and dissolved. Next, 0.15 g of polyoxyethylene nonyl phenyl ether was added and distilled water was further added so as to make the overall mass 6000 g. Furthermore, the mixture was colored with a small amount of Food blue No. 1 to prepare artificial urine.

2. Production of Absorbent Body and Absorbent Article

A sheet-shaped absorbent body having a size of length 40 cm×width 12 cm was produced using 10 g of the water-absorbent resin and 10 g of crushed pulp (produced by Leonia Co., Ltd; Leif lock) serving as the absorbent fibers, in conformity with the above-described working example "Manufacture of absorbent body". Next, approximately 0.6 g of water was spread over the entire obtained absorbent body using a vaporizer. Thereafter, an absorbent body for evaluation was produced by placing tissue paper having the same size as the absorbent body and having a basis weight of 16 g/m$^2$ on this absorbent body, and pressing the absorbent body while applying a load of 196 kPa to the entire absorbent body for 30 seconds. Further, polyethylene-polypropylene air-through type porous liquid permeable sheet having the same size as the absorbent body for evaluation and having a basis weight of 22 g/m$^2$ was disposed on an upper surface of the absorbent body for evaluation. Also, an absorbent article was prepared by disposing a polyethylene liquid impermeable sheet having the same size and the same basis weight as the polyethylene-polypropylene air-through type porous liquid permeable sheet on a lower surface of the absorbent body for evaluation and sandwiching the absorbent body for evaluation therebetween.

3. Evaluation Test

Next, the evaluation test below was performed using the above-described absorbent article.

(3-1) Permeation Time of Absorbent Article

The absorbent article was placed on a horizontal table, and a measurement instrument provided with a cylinder for liquid injection having an inner diameter of 3 cm was placed in a central portion of the absorbent article. Then, 50 mL of the artificial urine was introduced into the cylinder at once, and the amount of time until the artificial urine completely disappeared from the cylinder was measured using a stopwatch and the measured amount of time was denoted as a first permeation time (sec). Next, the cylinder was removed and the absorbent article was stored as it was, a similar operation was performed using the measurement instrument at the same position as in the first artificial urine injection 30 minutes and 60 minutes after the start of the first artificial urine injection, and a second permeation time (sec) and a third permeation time (sec) were measured. Then, the total time of the first to third injection was denoted as the total permeation time. It can be said that the shorter the permeation time is, the more preferable the sample is as the absorbent article.

(3-2) Return Amount 120 minutes after the start of the first test liquid injection in the measurement of the above-described permeation time, about 80 filter papers having 10 cm×10 cm whose mass (Wd(g)) was measured in advance were placed near an artificial urine injection position on the absorbent article, and a weight having a mass of 5 kg and whose bottom surface had a size of 10 cm×10 cm was placed thereon. After a load was applied for 5 minutes, the mass (We (g)) of the filter papers was measured, and an increased mass was denoted as a return amount (g) as the equation below. Note that it can be said that the smaller the return amount is, the more preferable the sample is as the absorbent article.

$$\text{Return amount (g)}=We-Wd$$

(3-3) Diffusion Length

A spreading dimension (cm) in the longitudinal direction of the absorbent article through which the artificial urine permeated was measured within 5 minutes after the measurement of the above-described return amount. Because a diffusion distance in the lateral direction of both ends of the liquid that spread from the central portion in which the artificial urine was introduced in the longitudinal direction varied, the maximum length of the distance by which the blue artificial urine spread in the longitudinal direction was measured as the diffusion length and the numerical values after the decimal points were rounded off.

Working Example 2 was the case where AQUA KEEP SA55SXII, whose absorption capacity was 55-fold and that was produced by SUMITOMO SEIKA CHEMICALS CO., LTD., was used as the water-absorbent resin, and Working Example 3 was the case where AQUA KEEP SA60SXII, whose absorption capacity was 60-fold, was used. The results are as follows.

TABLE 1

| Water-absorbent resin | Permeation time (sec) | | | | Return amount (g) | Diffusion length (cm) |
|---|---|---|---|---|---|---|
| | first | second | third | Total | | |
| Work. Ex. 2  SA55SXII | 19 | 16 | 24 | 59 | 30.5 | 19 |

TABLE 1-continued

| Water-absorbent resin | Permeation time (sec) | | | | Return amount (g) | Diffusion length (cm) |
|---|---|---|---|---|---|---|
| | first | second | third | Total | | |
| Work. Ex. 3 SA60SXII | 19 | 18 | 27 | 64 | 27.4 | 18 |

Accordingly, it is understood that the return amount was lower when the type with the type with the 60-fold absorption capacity was used, and the permeation time was shorter when the type with the 55-fold absorption capacity was used.

LIST OF REFERENCE NUMERALS

2: Conveying unit
3: Mixing unit
4: Chamber portion
5: Stacking portion
6: Suction unit
10: Absorbent body
31: Cylindrical body
33: Gap formation portion
333: Mesh member (plate-shaped member)
40: Internal space
52: Air circulation member
100: Material body
101: Absorbent fiber
102: Water-absorbent resin
531: Recessed portion

The invention claimed is:

1. A method for manufacturing an absorbent body for testing, the method comprising the following steps in sequence:
   a first step of obtaining a material body comprising an aggregate of absorbent fibers and a water-absorbent resin, wherein the water-absorbent resin is dispersively disposed in contact with the aggregate of the absorbent fibers;
   a second step of introducing a material body comprising an aggregate of absorbent fibers and a water-absorbent resin into a gap in a mixing unit that is formed between a first surface and a second surface, wherein the gap is smaller than a thickness of the material body comprising the aggregate of the absorbent fibers and the water-absorbent resin, recesses and protrusions being formed on at least one of the first surface and the second surface;
   a third step of applying a shearing force in the mixing unit to the material body in the mixing unit by moving the first surface relative to and parallel to the second surface in the mixing unit in order to crush and rub the material body and mix the aggregate of the absorbent fibers and the water-absorbent resin together; and
   a fourth step of causing the absorbent fibers and the water-absorbent resin that were mixed together while the material body was sheared and crushed to fall, and stacking the absorbent fibers and the water-absorbent resin by suctioning the absorbent fibers and the water-absorbent resin into a stationary recessed portion having a predetermined shape.

2. The method for manufacturing an absorbent body according to claim 1, wherein in the second step, the water-absorbent resin that is dispersively disposed in contact with the aggregate of the absorbent fibers is dispersively disposed on an upper surface of the absorbent fibers.

3. The method for manufacturing an absorbent body according to claim 1, wherein after the material body comprising the aggregate of the absorbent fibers and the water-absorbent resin are moved along the gap by a predetermined distance in the third step, the absorbent fibers and the water-absorbent resin that were mixed are caused to fall in the fourth step.

4. The method for manufacturing an absorbent body according to claim 3, wherein recesses and protrusions are formed on the first surface, and recesses and protrusions are formed on the second surface on a downstream side in a direction in which the material body comprising the aggregate of the absorbent fibers and the water-absorbent resin move.

5. The method for manufacturing an absorbent body according to claim 3, wherein a through hole is formed in the second surface on a downstream side in a direction in which the material body comprising the aggregate of the absorbent fibers and the water-absorbent resin move, and the absorbent fibers and the water-absorbent resin that were mixed are caused to fall from the through hole in the fourth step.

6. The method for manufacturing an absorbent body according to claim 1, wherein the first surface is formed by an outer circumferential surface of a rotatable cylindrical body, and the second surface is disposed facing the outer circumferential surface of the cylindrical body.

7. The method for manufacturing an absorbent body according to claim 6, wherein the through hole is formed at a site on the second surface that is positioned below the cylindrical body, and the absorbent fibers and the water-absorbent resin that were mixed are caused to fall from the through hole in the fourth step.

8. The method for manufacturing an absorbent body according to claim 1, wherein the absorbent fibers and the water-absorbent resin that were mixed are caused to fall into a closed space in the fourth step.

9. The method for manufacturing an absorbent body according to claim 8, wherein a shape of the closed space increases in size toward its lower end, and the recessed portion is formed into a shape corresponding to the shape of the lower end of the closed space.

10. The method for manufacturing an absorbent body according to claim 8, wherein the absorbent fibers and the water-absorbent resin that were mixed in a closed space are caused to fall through a mesh member in the fourth step.

11. The method for manufacturing an absorbent body according to claim 1, wherein a size of the absorbent body is 15 cm×10 cm to 80 cm×30 cm.

12. The method for manufacturing an absorbent body according to claim 1, further comprising a step of pressing the material body comprising the aggregate of the absorbent fibers into a flat shape before the first step.

13. The method for manufacturing an absorbent body according to claim 1, wherein in the second step, recesses and protrusions are formed on the first surface and recesses and protrusions are formed on the second surface, and in the third step, the material body comprising the aggregate of absorbent fibers and the water-absorbent resin are crushed due to shearing between recesses and protrusions on the first surface and recesses and protrusions on the second surface.

* * * * *